US010188592B2

(12) United States Patent
Carola et al.

(10) Patent No.: US 10,188,592 B2
(45) Date of Patent: Jan. 29, 2019

(54) 2-PYRONES

(71) Applicant: Merck Patent GmbH, Darmstadt (DE)

(72) Inventors: Christophe Carola, Bensheim (DE);
Tatjana Best, Hergerhausen (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/282,317

(22) Filed: Sep. 30, 2016

(65) Prior Publication Data

US 2017/0014325 A1 Jan. 19, 2017

Related U.S. Application Data

(62) Division of application No. 13/991,915, filed as application No. PCT/EP2011/005729 on Nov. 14, 2011, now Pat. No. 9,499,508.

(30) Foreign Application Priority Data

Dec. 10, 2010 (DE) .......................... 10 2010 054149

(51) Int. Cl.
| A61Q 19/06 | (2006.01) |
| A61Q 19/08 | (2006.01) |
| C07D 309/38 | (2006.01) |
| C07D 309/36 | (2006.01) |
| A23L 33/10 | (2016.01) |
| A61Q 17/04 | (2006.01) |
| A61K 8/49 | (2006.01) |
| A61K 8/06 | (2006.01) |

(52) U.S. Cl.
CPC .............. *A61K 8/498* (2013.01); *A23L 33/10* (2016.08); *A61K 8/062* (2013.01); *A61Q 17/04* (2013.01); *A61Q 19/06* (2013.01); *A61Q 19/08* (2013.01); *C07D 309/36* (2013.01); *C07D 309/38* (2013.01); *A23V 2002/00* (2013.01); *A61K 2800/522* (2013.01)

(58) Field of Classification Search
CPC ....... A23L 1/0315; A61K 8/498; A61Q 19/06; A61Q 19/08; C07D 309/36
See application file for complete search history.

(56) References Cited

U.S. PATENT DOCUMENTS

| 4,588,724 A | 5/1986 | Greenway, III et al. |
| 4,795,638 A | 1/1989 | Ayache et al. |
| 5,051,449 A | 9/1991 | Kligman |
| 5,585,386 A | 12/1996 | Rosenbaum |
| 5,750,570 A | 5/1998 | Voorhees et al. |
| 6,017,960 A | 1/2000 | Voorhees et al. |
| 6,150,403 A | 11/2000 | Biedermann et al. |
| 6,939,845 B2 | 9/2005 | Gautschi et al. |
| 7,537,775 B2 | 5/2009 | Coffindaffer et al. |
| 7,959,913 B2 | 6/2011 | Granger et al. |
| 8,226,933 B2 | 7/2012 | Granger et al. |
| 8,409,550 B2 | 4/2013 | Granger et al. |
| 2002/0035055 A1 | 3/2002 | Gautschi et al. |
| 2004/0043044 A1 | 3/2004 | Granger et al. |
| 2004/0175347 A1* | 9/2004 | Bissett ................... A61K 8/347 424/70.13 |
| 2004/0220137 A1 | 11/2004 | Sauermann |
| 2005/0037099 A1 | 2/2005 | Markman et al. |
| 2006/0165741 A1 | 7/2006 | Coffindaffer et al. |
| 2008/0234342 A1 | 9/2008 | Granger et al. |
| 2011/0206626 A1 | 8/2011 | Granger et al. |
| 2012/0258061 A1 | 10/2012 | Granger et al. |

FOREIGN PATENT DOCUMENTS

| DE | 4231465 A1 | 3/1994 |
| DE | 10133202 A1 | 1/2003 |
| EP | 0487404 A1 | 5/1992 |
| EP | 0672406 A1 | 9/1995 |
| EP | 0841063 A1 | 5/1998 |
| EP | 0866693 A1 | 9/1998 |
| EP | 1167362 A1 | 1/2002 |
| GB | 2410435 A | 8/2005 |
| JP | 07-285913 | 10/1995 |
| JP | 08-040894 A | 2/1996 |
| JP | 10-182626 A | 7/1998 |
| JP | 2003510241 A | 3/2003 |
| JP | 2004024298 A | 1/2004 |
| JP | 2004175780 A | 6/2004 |
| JP | 2006206467 A | 8/2006 |
| JP | 2006342144 A | 12/2006 |
| JP | 2007284435 A | 11/2007 |
| JP | 2008528488 A | 7/2008 |
| JP | 2009023975 A | 2/2009 |
| WO | 9304665 A1 | 3/1993 |

(Continued)

OTHER PUBLICATIONS

Marrison et al., "Suzuki Cross-Coupling Approaches to the Synthesis of Bioactive 3-Substituted and 5-Substituted-4-methoxy-6-methyl-2-pyrones," Bioorg. & Med. Chem. Letters (2003); 13: pp. 2667-2671.*

Moreno-Mañas et al., "Palladium-Catalyzed C-Alkylations of the Highly Acidic and Enolic Triacetic Acid Lactone. Mechanisms and Stereochemistry," J. Org. Chem. 1988, 53; pp. 5328-533. (Year: 1988).*

English Translation of Abstract for WO9304665A1 dated Mar. 18, 1993.

English Translation of Abstract for JP2004024298A dated Jan. 29, 2004.

English Translation of Abstract for JP2006206467A dated Aug. 10, 2006.

English Translation of Abstract for DE4231465A1 dated Mar. 24, 1994.

English Translation of Abstract for EP0866693A1 dated Sep. 30, 1998.

(Continued)

*Primary Examiner* — Sreenivasan Padmanabhan
*Assistant Examiner* — Jody L Karol
(74) *Attorney, Agent, or Firm* — Millen White Zelano and Branigan, PC; John Sopp

(57) ABSTRACT

The present invention relates to the use of compounds of the formula (I) for the care, preservation or improvement of the general condition or appearance of the skin or hair, and to preparations comprising compounds of the formula (I).

12 Claims, No Drawings

(56) References Cited

FOREIGN PATENT DOCUMENTS

| WO | 9319743 | A1 | 10/1993 |
| WO | 97/35565 | A1 | 10/1997 |
| WO | 0202074 | A2 | 1/2002 |
| WO | 2007125832 | A1 | 11/2007 |

OTHER PUBLICATIONS

Rahul R. Nagawade et al. "Synthesis of new series of 1-Aryl-1,4-dihydro-4-oxo-6-methyl pyridazine-3-carboxylic acid as potential antibacterial agents" European Journal of Medicinal Chemistry 40 (2005) pp. 1325-1330.

Mitchell L. Shlossman "Treated Pigments—New Ways to Impart Color on the Skin" Cosmetics & Toiletries, vol. 105, (Feb. 1990), pp. 53-64.

Katarzyna Lemanska, et al. "The Influence of pH on Antioxidant Properties and the Mechanism of Antioxidant Action of Hydroxyflavones" Free Radical Biology & Medicine, vol. 31, No. 7, pp. 869-881 [2001].

Catherine A. Rice-Evans, et al. "Antioxidant Properties of Phenolic Compounds" Trends in Plant Science, Elsevier Science Ltd., vol. 2, No. 4 [Apr. 1997] pp. 152-159.

Katarzyna Lemanska, et al. "Effect of Substitution Pattern on TEAC Antioxidant Activity of Mono- and Dihydroxyflavones" Current Topics in Biophysics [2000], 24(2), pp. 101-108.

Official Action related to the corresponding Japanese Patent Application No. 2013542391 dated Jul. 6, 2015.

Jun Zhu, et al., "Syntheses and Biological Activities of Pyranyl-substituted Cinnamates" Biosci, Biotechnol. Biochem., [2001], vol. 65, No. 1, pp. 161-163.

Desen Zheng, et al., "Molecular and biochemical characterization of three aromatic polyketide synthase genes from Rubus Idaeus" Plant Molecular Biology, [2001], Vo. 46, pp. 1-15.

* cited by examiner

2-PYRONES

The present invention relates to the use of compounds of the formula (I) for the care, preservation or improvement of the general condition or appearance of the skin or hair, and to preparations comprising compounds of the formula (I).

The human skin is subject to certain ageing processes, some of which are attributable to intrinsic processes (chronoageing) and some of which are attributable to exogenous factors (environmental, for example photoageing). In addition, temporary or even lasting changes to the skin picture can occur, such as acne, greasy or dry skin, keratoses, rosaceae, light-sensitive, inflammatory, erythematous, allergic or autoimmune-reactive reactions, such as dermatoses and photodermatoses.

The exogenous factors include, in particular, sunlight or artificial radiation sources having a comparable spectrum, and compounds which can be formed by the radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen or nitrogen compounds which interfere with the natural physiology or morphology of the skin.

The influence of these factors can result, inter alia, in direct damage to the DNA of the skin cells and to the collagen, elastin or glycosaminoglycan molecules of the extracellular matrix, which are responsible for the strength of skin. In addition, the signal transduction chains, which are terminated by the activation of matrix-degrading enzymes, may be affected. Important representatives of these enzymes are the matrix metalloproteinases (MMPs, for example collagenases, gelatinases, stromelysins), whose activity is additionally regulated by TIMPs (tissue inhibitor of matrix metalloproteinases).

The consequences of the above-mentioned ageing processes are thinning of the skin, weaker interlacing of epidermis and dermis, reduction in the number of cells and the supplying blood vessels. This results in the formation of fine lines and wrinkles, the skin becomes leathery, and pigment defects can occur.

The same factors also act on hair, where damage can likewise occur. The hairs become brittle, less elastic and dull. The surface structure of the hairs is damaged.

Cosmetic or dermatological care products having properties which are claimed to counter the above-described or comparable processes or reduce or reverse the harmful consequences thereof are frequently distinguished by the following specific properties—free-radical-scavenging, antioxidative, inflammation-inhibiting or humectant. They prevent or reduce, inter alia, the activity of matrix-degrading enzymes or regulate the new synthesis of collagen, elastin or proteoglycans.

The use of antioxidants or free-radical scavengers in cosmetic preparations is adequately known per se. Thus, the use of the antioxidative vitamin E in sunscreen formulations is usual. Nevertheless, the effect achieved is even here well short of the hoped-for effect.

Vitamin A and vitamin A derivatives, such as retinoic acid, retinol and retinol esters, act on the differentiation of epithelial cells and are therefore employed for the prophylaxis and treatment of numerous phenomena which impair the skin state; for example use against acne, psoriasis, age spots, skin discoloration and wrinkles has been described (cf., for example, WO 93/19743, WO 02/02074).

Cellulite denotes the dimpling of the skin which occurs in many women, principally in the area of the thigh, buttocks, but also on the stomach and upper arms. Many affected women suffer mentally from this aesthetic problem. Although the cause of cellulite is not fully known to date, it appears to be principally attributable to the local accumulation of fat and the anatomical nature of the subcutaneous fatty tissue. Histological studies on subcutaneous fatty tissue from women and men have shown that the fat lobules in women are larger and arranged more vertically than in men. They can expand outwardly against the dermis and thus produce the dimples and bumps that are characteristic of cellulite. Owing to the different distribution of alpha- and beta-adrenergic receptors, the subcutaneous fat deposits of the thigh in women usually also have a lower lipolytic activity than the fat deposits on the stomach or other body regions. The increase in lipolysis or the reduction in fat deposits in these specific areas can therefore contribute to reducing cellulite or preventing it.

The best-known and used method for lipolysis stimulation consists in the inhibition of phosphodiesterase in order to suppress or at least minimise the breakdown of cyclic AMP (cAMP), since cAMP acts as activator for lipolysis. Known active compounds for topical application for the treatment of cellulite by lipolysis are, for example, xanthine analogues, such as theobromine, aminophylline, caffeine or theophylline.

Further known methods for the treatment of cellulite are based on the stimulation of adenylate cyclase for increasing the cAMP concentration (beta-adrenergic agonists) or on the blocking of antipolytic deactivation of adenylate cyclase (alpha-2-adrenergic antagonists). For example, isoproterenol is a known beta-adrenergic stimulator (U.S. Pat. No. 4,588,724B1).

It is furthermore known that the use of certain oil-soluble plant extracts also has a slimness effect. Examples of such plant extracts are the extracts from common ivy (*Hedera helix*), arnica (*Arnica montana*), rosemary (*Rosmarinus officinalis* N), marigold (*Calendula officinalis*), sage (*Salvia officinalis* N), ginseng (*Panax ginseng*), *Hypericum perforatum*, *Ruscus aculeatus*, *Filipendula ulmaria* L and *Ortosifon stamincus* Benth.

Retinoids can also reduce the signs of cellulite if they are applied topically (EP-A-866 693; U.S. Pat. No. 5,051,449). They make the skin surface flatter and smoother.

Owing to the constantly increasing demand for cosmetic active ingredients for the preventative treatment of human skin and human hair against ageing processes and harmful environmental influences, the object of the present invention was to provide novel cosmetic active ingredients and/or medicament active ingredients which exhibit the effects already mentioned at the outset, are sufficiently oxidation- and photostable and can readily be formulated.

The aim of the present invention is therefore the provision of compounds for the care, preservation or improvement of the general condition or appearance of the skin or hair.

Surprisingly, it has now been found that certain 2-pyrone derivatives can be employed as antiageing or anticellulite active compounds.

In the prior art, pyrone derivatives are known for various applications. DE 4231465 A1 describes the use of various acyloxypyranones, such as 4-acetoxy-6-methyl-2H-2-pyranone or 4-butyroxy-6-methyl-2H-2-pyranone, as activators for inorganic percompounds which can be employed as bleaches in detergents.

EP 0672406 A1 discloses pyrone derivatives which stimulate hair growth and slow hair loss. Mention is made, for example, of the compounds 5,6-dihydro-6-methyl-2H-pyran-2-one, 4-methoxy-6-(2-phenylethenyl)2H-pyran-2-one and 4-methoxy-6-[2-(4-methoxyphenyl)ethenyl]2H-pyran-2-one.

EP 1167362 A1 discloses pyrone derivatives as fragrant lactones which can form as cleavage products from fragrance precursor compounds which can be used in perfumed products, such as washing compositions, cleaning products or body-care products.

The use of various pyrone derivatives as pesticides for the treatment of plants against fungal infestation is disclosed in GB 2410435 A.

JP 2006-206467 A describes that certain pyrone derivatives can be used for increasing melanogenesis.

JP 2004-024298 A discloses pyrone derivatives for use in foaming deodorant active compounds for aerosols.

The present invention relates firstly to the use of at least one compound of the formula (I)

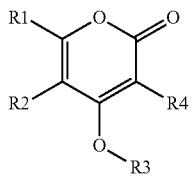

where
R1 stands for a straight-chain or branched $C_1$- to $C_{20}$-alkyl group,
R2 stands for
H or
straight-chain or branched $C_1$- to $C_{20}$-alkyl group,
R4 stands for
H,
straight-chain or branched $C_1$- to $C_{20}$-alkyl group or
straight-chain or branched $C_2$- to $C_{20}$-alkenyl group having one or more double bonds,
R3 stands for a radical selected from
H,
straight-chain or branched $C_1$- to $C_{20}$-alkyl group,
straight-chain or branched $C_2$- to $C_{20}$-alkenyl group having one or more double bonds, where the alkenyl group may also be substituted by one or more saturated or unsaturated $C_3$- to $C_{12}$-cycloalkyl groups,
straight-chain or branched $C_2$- to $C_{20}$-alkynyl group having one or more triple bonds,
saturated or unsaturated $C_3$- to $C_{12}$-cycloalkyl group, where the rings may in each case also be bridged by —$(CH_2)_n$— groups where n=1 to 3,
an acyl radical of the formula —C(=O)—R6,
R6 stands for
straight-chain or branched $C_1$- to $C_{20}$-alkyl group,
a radical of the formula (II)

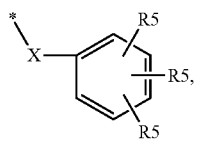

in which X stands for straight-chain or branched $C_1$- to $C_6$-alkylene or straight-chain or branched $C_2$- to $C_6$-alkenylene and the radicals R5 are selected, independently of one another, from H, OH, straight-chain or branched $C_1$- to $C_6$-alkyl or straight-chain or branched O—($C_1$- to $C_6$-alkyl),
for the care, preservation or improvement of the general condition or appearance of the skin or hair.

The compounds of the formula (I) are preferably used for the care, preservation or improvement of the general condition or appearance of the skin.

For the purposes of the present invention, the term "compound of the formula (I)" basically also encompasses the salts of the compounds of the formula (I). The preferred salts here include, in particular, alkali-metal and alkaline-earth metal salts and ammonium salts, but in particular sodium and potassium salts.

In a preferred embodiment of the present invention, the at least one compound of the formula (I) is used for the prevention, reduction or combating of cellulite or signs of cellulite and/or for the reduction of local fat accumulation, particularly preferably for the stimulation of lipolysis.

The term lipolysis here denotes the mobilisation of fat in the adipocytes of the fatty tissue by hydrolytic cleavage.

The compounds of the formula (I) are suitable, for example, for positively influ-encing the external appearance of the skin and the figure. Besides the reduction of cellulite, a slimming effect can also be achieved by lipolysis. Overall, this results in the skin appearing smoother and tauter.

In a further preferred embodiment of the present invention, the at least one compound of the formula (I) is used for prophylaxis against or combating of time- and/or light-induced ageing processes of the skin or hair.

A particularly preferred use is prophylaxis against or reduction of skin unevenness, such as wrinkles, fine lines, rough skin or large-pored skin.

A further particularly preferred use of the compounds of the formula (I) is the use for the prophylaxis and/or prevention of premature skin ageing, in particular for the prophylaxis and/or prevention of light- or ageing-induced wrinkling of the skin, for the reduction of pigmentation and keratosis actinica in the cosmetic sense.

Particular preference is given here in accordance with the invention to, in particular, the non-therapeutic use of the compounds of the formula (I).

Furthermore, the compounds of the formula (I) can also be used as medicament active ingredient for the prophylaxis and/or treatment of all diseases associated with normal ageing or light-induced ageing of the skin, and for the prophylaxis and/or treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplasia, leukoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, and for the prophylaxis and/or treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare.

The use according to the invention of 2-pyrone derivatives of the general formula I in preparations, both in the cosmetic sense and also as medicament active ingredient, offers, inter alia, protection against damage caused directly or indirectly by UV radiation or processes caused by reactive compounds, such as, for example, skin ageing, loss of skin moisture, loss of skin elasticity, formation of wrinkles or lines or of pigment defects or age spots.

Furthermore possible is the non-therapeutic use of the above-mentioned compounds or preparations thereof for the prevention of undesired changes in the skin picture, such as, for example, acne or greasy skin, keratoses, light-sensitive, inflammatory, erythematous, allergic or autoimmune-reactive reactions in the cosmetic sense, and to the use as medicament active ingredient for the said changes in the skin picture.

Compounds of the formula (I) can be used, for example, for preventative treatments of inflammation and allergies of the skin and in certain cases for preventing certain types of cancer. Compounds of the formula I are particularly suitable as medicament active ingredient for the treatment of inflammation, allergies and irritation, in particular of the skin. It is furthermore possible to prepare preparations which act as vein tonic, as cuperose inhibitor, as inhibitor of chemical, physical or actinic erythemas, as agent for the treatment of sensitive skin, as decongestant, as dehydration agent, as slimming agent, as anti-wrinkle agent, as stimulators of the synthesis of components of the extracellular matrix, as strengthening agent for improving skin elasticity, and as anti-ageing agent.

However, the compounds of the formula (I) and preparations comprising at least one compound of the formula (I) also serve for calming sensitive and irritated skin, for the preventative regulation of collagen, hyaluronic acid and elastin synthesis, stimulation of DNA synthesis, in particular in the case of deficient or hypoactive states of the skin, regulation of the transcription and translation of matrix-degrading enzymes, in particular of MMPs, increasing cell regeneration and regeneration of the skin, increasing the skin's own protective and repair mechanisms for DNA, lipids and/or proteins.

In formula (I), R1 preferably stands for a straight-chain or branched $C_1$- to $C_6$-alkyl group, particularly preferably for methyl.

R2 preferably stands for H or a straight-chain or branched $C_1$- to $C_6$-alkyl group, particularly preferably for H.

R4 preferably stands for H or a straight-chain or branched $C_2$- to $C_{20}$-alkenyl group having one or more double bonds.

In a particularly preferred embodiment of the present invention, R4 stands for a straight-chain or branched $C_2$- to $C_{20}$-alkenyl group having one or more double bonds, in particular a straight-chain or branched $C_6$- to $C_{14}$-alkenyl group having one or more double bonds.

In a further particularly preferred embodiment of the present invention, R4 stands for H.

If R4 stands for H, a possible and preferred embodiment of the present invention thus arises through the compound of the formula (I) standing for a compound of the formula (III)

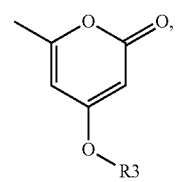

(III)

in which R3 is as defined above and below.

R3 preferably stands for a radical selected from

H, straight-chain or branched $C_1$- to $C_{20}$-alkyl group, straight-chain or branched $C_2$- to $C_{20}$-alkenyl group having one or more double bonds, where the alkenyl group may also be substituted by one or more saturated or unsaturated cyclohexyl groups, an acyl radical of the formula —C(=O)—R6.

The radicals R5 in formula (I) are preferably selected, independently of one another, from H, OH or straight-chain or branched O—($C_1$- to $C_6$-alkyl). The radicals R5 are particularly preferably selected, independently of one another, from H, OH and $OCH_3$. In a very particularly preferred embodiment of the present invention, two R5 stand for H and one R5 stands for $OCH_3$ In formula (II), X preferably stands for $CH_2CH_2$ or CH=CH.

In a particularly preferred embodiment of the present invention, the compound of the formula (I) is selected from the compounds of the formula (Ia) to (Ij)

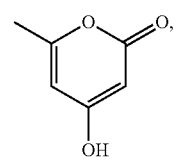

(Ia)

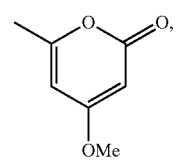

(Ib)

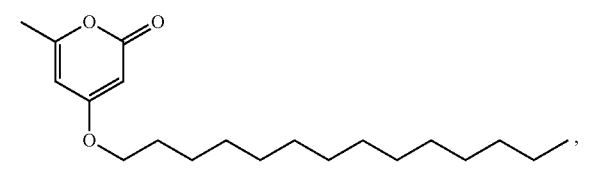

(Ic)

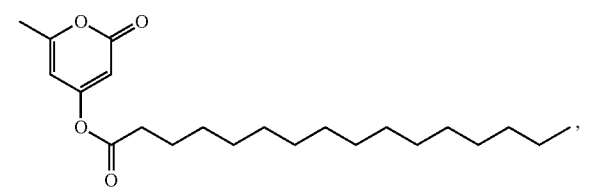

(Id)

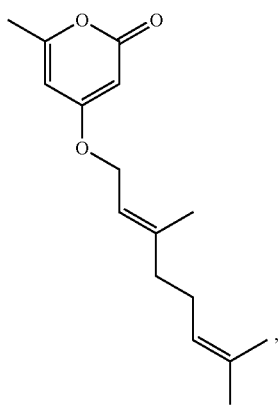
(Ie)

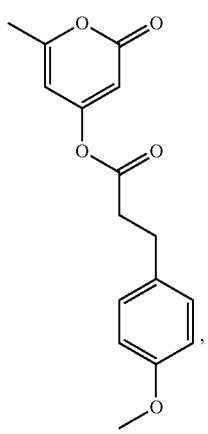
(If)

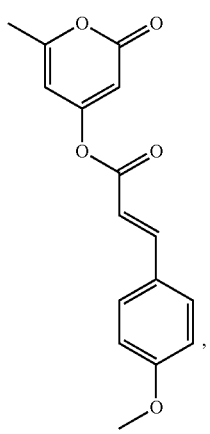
(Ig)

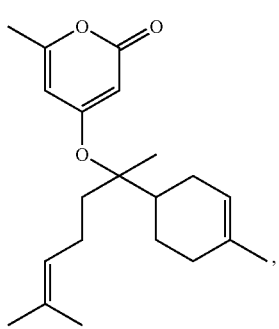
(Ih)

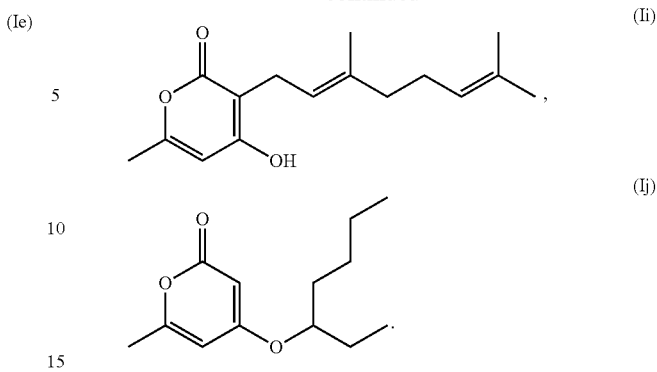
(Ii), (Ij)

For use for prophylaxis against or for combating time- and/or light-induced ageing processes of the skin or hair, the compounds of the formula (Ia) and (Ii) are particularly advantageous.

For use for the prevention, reduction or combating of cellulite or signs of cellulite and/or for the reduction of local fat accumulation, the compounds of the formula (Ib) and (Ij) are particularly advantageous.

It is thought, without being tied to this theory, that the compounds of the formula (I) contribute to reducing the signs of cellulite through the interaction of various factors, for example:

(1) Stimulation of the fibroblasts to produce larger amounts of basic substance (glycoproteins and glycosaminoglycans) in which the collagen fibres are distributed and which slide past one another when the skin is stretched.

(2) Increase of the proliferative and metabolic activity of the fibroblasts, causing fresh collagen to be deposited in the upper dermis and the skin to be compacted.

(3) Stimulation of the blood flow and promotion of the formation of vascular tissue (angiogenesis), causing the circulation and the activity of other cell types of the dermis to be improved.

The use of compounds of the formula (I) enables a tauter, thicker and healthier dermis to be achieved, which restricts the mobility of the readily deformable fat lobules and thus prevents the latter from projecting out of the subcutaneous fat layer into the overlying dermis.

It is thought that the compounds of the formula I also act as enzyme inhibitors. They are thought to inhibit protein kinases, elastase, aldose reductase and hyaluronidase. Furthermore, they are thought to inhibit non-specifically catechol O-methyl transferase, causing the amount of available catecholamines and thus the vascular strength to be increased. Furthermore, they are thought to inhibit AMP phosphodiesterase.

Owing to these properties, the compounds of the formula (I) are in general suitable for immune protection and for the protection of DNA and RNA. In particular, the preparations are suitable for the protection of DNA and RNA against oxidative attack, against free radicals and against damage due to radiation, in particular UV radiation. A further advantage of the preparations according to the invention is cell protection, in particular protection of Langerhans cells against damage due to the above-mentioned influences.

In particular, the compounds of the formula (I) are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplasia, leukoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammations which are not associated with a defect in keratinisation, for the treatment of all benign or malignant excrescence of the dermis or epidermis, which may be of viral origin, such as verruca vulgaris. verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or precarcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and non-insulin-dependent diabetes, for the treatment of skin problems caused by UV radiation.

For the purposes of the present invention, a straight-chain or branched $C_1$- to $C_6$-alkyl group is an alkyl radical having 1 to 6 C atoms, for example methyl, ethyl, isopropyl, propyl, butyl, sec-butyl or tert-butyl, pentyl, isopentyl, 1-, 2- or 3-methylbutyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, 1,1-, 1,2-, 1,3-, 2,2-, 2,3- or 3,3-dimethylbutyl, 1- or 2-ethylbutyl, 1-, 2-, 3- or 4-methylpentyl or hexyl.

Besides the radicals listed above, a $C_1$- to $C_{20}$-alkyl group can also be, for example, heptyl, 1-ethylpentyl, octyl, 1-ethylhexyl, nonyl, decyl, undecyl, dodecyl, tridecyl, tetradecyl, pentadecyl, hexadecyl, heptadecyl, octadecyl, nonadecyl or eicosyl.

Correspondingly, a $C_1$- to $C_6$-alkylene radical is, for example, methylene, ethylene, propylene, butylene, pentylene or hexylene.

In accordance with the invention, an alkenyl group can contain one or more double bonds. A straight-chain or branched $C_2$- to $C_{20}$-alkenyl group is, for example, allyl, vinyl, propenyl, 2- or 3-butenyl, isobutenyl, sec-butenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl, isopentenyl, hexenyl, heptenyl or octenyl, —$C_9H_{17}$, —$C_{10}H_{19}$ to —$C_{20}H_{39}$.

Examples of a $C_2$- to $C_6$-alkenylene radical are ethenylene, propenylene, 2- or 3-butenylene, 1-, 2-, 3- or 4-pentenylene or hexenylene.

An alkynyl group can contain one or more triple bonds. Examples of a branched or unbranched $C_2$- to $C_{20}$-alkynyl group are ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$.

A $C_3$- to $C_{12}$-cycloalkyl group in the sense of the invention denotes saturated and partially unsaturated non-aromatic cyclic hydrocarbon groups which contain 3 to 12 C atoms and may also be bridged by —$(CH_2)$— groups, where n=1, 2 or 3. The bonding to the respective radical can take place via any ring member of the cycloalkyl group. Examples of suitable cycloalkyl radicals are cyclopropyl, cyclobutyl, cyclopentyl, cyclohexyl, cycloheptyl, cyclooctyl, cyclopentenyl, cyclopentadienyl, cyclohexenyl and cyclooctadienyl.

A cyclic alkyl radical having 6 C atoms is preferably cyclohexyl or cyclohexenyl.

The compounds of the formula (I) can be prepared by a ring-closure reaction starting from the corresponding β-ketoesters and subsequent deacylation.

For example, compounds of the formula (Ia) can be synthesised in a two-step reaction as depicted in the following scheme (Nagawade et al. 2005, European Journal of Medicinal Chemistry 40: 1325):

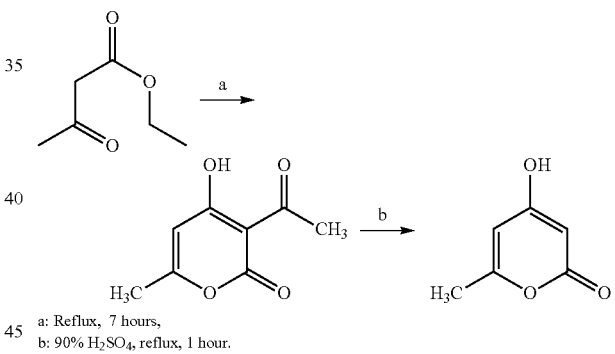

a: Reflux, 7 hours,
b: 90% $H_2SO_4$, reflux, 1 hour.

The corresponding substituents can then be introduced by suitable alkylation reactions and subsequent etherification or esterification reactions which are known to the person skilled in the art. Starting from compounds of the formula (Ia), compounds of the formula (Ib), (Ic), (Ie) or (Ij) can be prepared, for example by etherification with the aid of dimethyl sulfate, bromotetradecane, (E)-1-bromo-3,7-dimethylocta-2,6-diene or bromoheptane. The compounds of the formula (Id), (If) or (Ig), for example, can be prepared starting from compound (Ia) by esterification using the corresponding acid chlorides.

The compounds of the formula (Ia) (Alfa Aesar) and (Ib) (Aldrich) and the other reactants in the synthesis are commercially available or accessible by syntheses which are known to the person skilled in the art from the literature. The person skilled in the art is presented with no difficulties here in selecting the suitable reaction conditions, such as solvents or temperature.

Examples of possible solvents are acetonitrile, dimethylformamide, methanol, pyridine or toluene.

The present invention furthermore relates to a cosmetic or pharmaceutical preparation or a food comprising at least one compound of the formula (I) and at least one vehicle which is suitable for topical applications or for foods. Preferred embodiments of the radicals R1 to R6 and X of the formula (I) are defined here as described above.

The preparations here are usually preparations which can be applied topically, for example cosmetic or dermatological formulations or medical products. In this case, the preparations comprise a cosmetically or dermatologically suitable vehicle and, depending on the desired property profile, optionally further suitable ingredients. In the case of pharmaceutical preparations, the preparations in this case comprise a pharmaceutically tolerated vehicle and optionally further pharmaceutical active compounds. The preparations can also be foods. In accordance with the invention, this term also includes food supplements or "functional food". In this case, the preparations comprise a vehicle which is suitable for foods.

In the sense of the present invention, the term composition or formulation is also used synonymously alongside the term preparation.

"Can be applied topically" in the sense of the invention means that the preparation is applied externally and locally, i.e. that the preparation must be suitable for, for example, application to the skin.

The preparations may include or comprise, essentially consist of or consist of the said requisite or optional constituents. All compounds or components which can be used in the preparations are either known and commercially available or can be synthesised by known processes.

The preparation is preferably a cosmetic or pharmaceutical preparation; the preparation is particularly preferably a cosmetic preparation.

If the preparation is to be employed for combating cellulite or for reducing local accumulation of fat, a preparation in the form of a food, food supplement or "functional food" is also advantageous. Oral administration of the preparation results in weight loss in this case.

The at least one compound of the formula (I) is typically employed in the preparations according to the invention in amounts of 0.01 to 20% by weight, preferably in amounts of 0.05 to 10% by weight, particularly preferably in amounts of 0.1% by weight to 5% by weight and very particularly preferably in amounts of 0.5 to 2% by weight, based on the total amount of the preparation. The person skilled in the art is presented with absolutely no difficulties here in selecting the amounts appropriately depending on the intended action of the preparation and the given conditions, such as age, weight or skin condition.

In the case of oral administration, amounts of at least 0.05 mg/day to 20 mg/day are typically necessary. The dosage can also be adapted corresponding to the measured change in cellulite or fat content. In any case, the dosage is dependent on the weight, age and gender of the individual to be treated.

Besides the compounds of the formula (I), the preparations according to the invention additionally also comprise at least one UV filter.

Organic UV filters, so-called hydrophilic or lipophilic sun-protection filters, which are effective in the UVA region and/or UVB region and(/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO-93/04665. Further examples of organic filters are indicated in the patent application EP-A 0 487 404. The said UV filters are usually named below in accordance with INCI nomenclature.

Particularly suitable for a combination are:

para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed under the name "Uvinul P25" by BASF.

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", "Uvinul N539" from BASF, Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl) benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl 4'-aminobenzalmalonate)-s-triazine or 2,4,6-tris(biphenyl)-1,3,5-triazine. marketed as Tinosorb A2B by BASF, 2,2'-[6-(4-methoxyphenyl)-1,3,5-triazine-2,4-diyl]bis[5-(2-ethylhexyl)oxy]phenol, marketed as Tinosorb S by BASF, N2,N4-bis[4-[5-(1,1-dimethylpropyl)-2-benzoxazolyl]phenyl]-N6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: Ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl) benzoxazol-2-yl(4-phenyl) imino]-6-(2-ethylhexyl)imino-1,3,5-triazine, for example marketed by Sigma 3V under the name Uvasorb K2A, and mixtures comprising this.

Piperazine derivatives, such as, for example, the compound

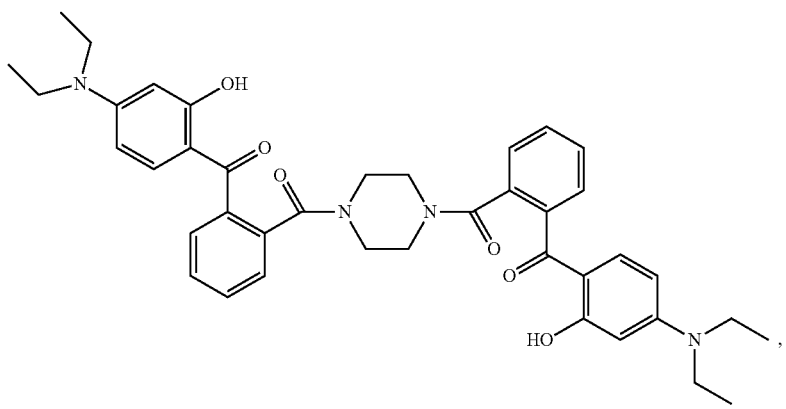 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures

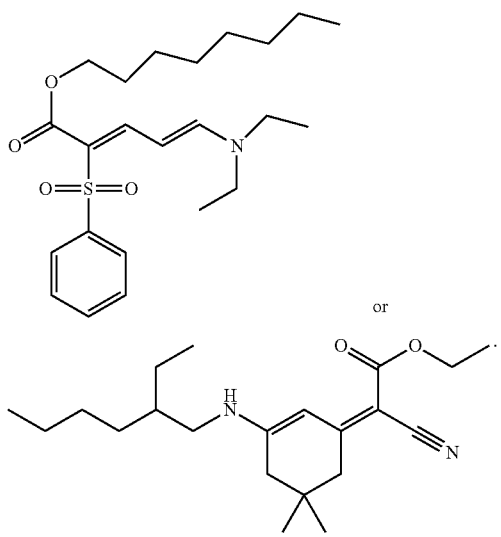

It is also possible to use UV filters based on polysiloxane copolymers having a random distribution in accordance with the following formula, where, for example, a=1,2; b=58 and c=2,8:

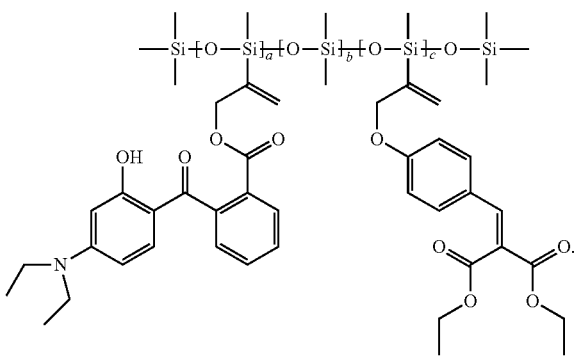 [SMILES: C=C(COC(=O)c1ccccc1C(=O)c1ccc(N(CC)CC)cc1O)[Si](C)(O[Si](C)(C)C)O[Si](C)(C)O[Si](C)(O[Si](C)(C)C)C(=C)COc1ccc(C=C(C(=O)OCC)C(=O)OCC)cc1]

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-bis[5-1 (dimethylpropyl)benzoxazol-2-yl(4-phenyl) imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Besides the compounds of the formula I and the optionally organic UV filters, as described above, the preparations may comprise further inorganic UV filters, so-called particulate UV filters.

These combinations with particulate UV filters are possible both as powder and also as dispersion or paste of the following types.

Preference is given here both to those from the group of the titanium dioxides, such as, for example, coated titanium dioxide (for example Eusolex® T-2000, Eusolex® T-AQUA, Eusolex® T-AVO, Eusolex® T-OLEO), zinc oxides (for example Sachtotec®), iron oxides or also cerium oxides and/or zirconium oxides.

Furthermore, combinations with pigmentary titanium dixoxide or zinc oxide are also possible, where the particle size of these pigments are greater than or equal to 200 nm, for example Hombitan® FG or Hombitan® FF-Pharma.

It may furthermore be preferred for the preparations to comprise inorganic UV filters which have been aftertreated by conventional methods, as described, for example, in Cosmetics & Toiletries, February 1990, Vol. 105, pp. 53 64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

Particulate UV filters which are preferably employed here are:

untreated titanium dioxides, such as, for example, the products Microtitanium Dioxide MT 500 B from Tayca; titanium dioxide P25 from Degussa, Aftertreated micronised titanium dioxides with aluminium oxide and silicon dioxide aftertreatment, such as, for example, the product "Microtitanium Dioxide MT 100 SA from Tayca; or the product "Tioveil Fin" from Uniqema, Aftertreated micronised titanium dioxides with aluminium oxide and/or aluminium stearate/laurate aftertreatment, such as, for example, Microtitanium Dioxide MT 100 T from Tayca, Eusolex T-2000 from Merck, Aftertreated micronised titanium dioxides with iron oxide and/or iron stearate aftertreatment, such as, for example, the product "Microtitanium Dioxide MT 100 F" from Tayca, Aftertreated micronised titanium dioxides with silicon dioxide, aluminium oxide and silicone aftertreatment, such as, for example, the product "Microtitanium Dioxide MT 100 SAS", from Tayca, Aftertreated micronised titanium dioxides with sodium hexametaphosphates, such as, for example, the product "Microtitanium Dioxide MT 150 W" from Tayca.

The treated micronised titanium dioxides employed for the combination may also be aftertreated with:

octyltrimethoxysilanes; such as, for example, the product Tego Sun T 805 from Degussa, silicon dioxide; such as, for example, the product Parsol T-X from DSM, aluminium oxide and stearic acid; such as, for example, the product UV-Titan M160 from Sachtleben, aluminium and glycerine; such as, for example, the product UV-Titan from Sachtleben, aluminium and silicone oils, such as, for example, the product UV-Titan M262 from Sachtleben, sodium hexametaphosphate and polyvinylpyrrolidone, polydimethylsiloxanes, such as, for example, the product 70250 Cardre UF TiO2SI3" from Cardre, polydimethylhydrogenosiloxanes, such as, for example, the product Microtitanium Dioxide USP Grade Hydrophobic" from Color Techniques.

The combination with the following products may furthermore also be advantageous:

Untreated zinc oxides, such as, for example, the product Z-Cote from BASF (Sunsmart), Nanox from Elementis Aftertreated zinc oxides, such as, for example, the following products:

"Zinc Oxide CS-5" from Toshibi (ZnO aftertreated with polymethylhydrogenosiloxanes)

Nanogard Zinc Oxide FN from Nanophase Technologies

"SPD-Z1" from Shin-Etsu (ZnO aftertreated with a silicone-grafted acrylic polymer, dispersed in cyclodimethylsiloxanes "Escalol Z100" from ISP (aluminium oxide-aftertreated ZnO dispersed in an ethylhexyl methoxycinnamate/PVP-hexadecene/methicone copolymer mixture)

"Fuji ZNO-SMS-10" from Fuji Pigment (ZnO aftertreated with silicon dioxide and polymethylsilesquioxane);

Untreated cerium oxide micropigment, for example with the name "Colloidal Cerium Oxide" from Rhone Poulenc Untreated and/or aftertreated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide. zinc oxide mixtures, such as, for example, the product UV-Titan M261 from Sachtleben.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form.

The capsules in preparations to be employed in accordance with the invention are preferably present in amounts which ensure that the encapsulated UV filters are present in the preparation in the percent by weight ratios indicated above.

The preparations described, which in accordance with the invention comprise the at least one compound of the formula (I), may furthermore also comprise coloured pigments, where the layer structure of the pigments is not limited.

The coloured pigment should preferably be skin-coloured or brownish on use of 0.5 to 5% by weight. The selection of a corresponding pigment is familiar to the person skilled in the art.

Preferred preparations may likewise comprise at least one further cosmetic active compound, for example selected from antioxidants, anti-ageing, anti-wrinkle, anti-dandruff, anti-acne, anti-cellulite active compounds, deodorants, skin-lightening active compounds, self-tanning substances or vitamins.

The protective action of preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles, (for ecample urocanic acid) and derivatives thereof, peptides, such as D,L-carnosine, D-carnosine, L-carnosine and derivatives thereof (for example anserine), carotinoids, carotenes (for example α-carotene, (3-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, α-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to mol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA, pentasodium ethylenediamine tetramethylene phosphonate and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxy-anisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the formulae A or B

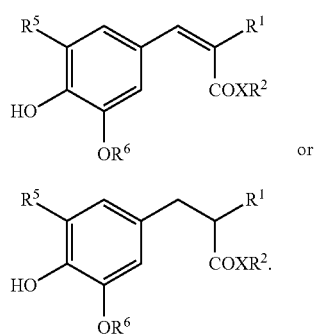

in which
$R^1$ can be selected from the group —C(O)CH$_3$, —CO$_2R^3$, —C(O)NH$_2$ and —C(O)N(R$^4$)$_2$,
X denotes O or NH,'
$R^2$ denotes linear or branched alkyl having 1 to 30 C atoms,
$R^3$ denotes linear or branched alkyl having 1 to 20 C atoms,
$R^4$ in each case, independently of one another, denotes H or linear or branched alkyl having 1 to 8 C atoms,
$R^5$ denotes H, linear or branched alkyl having 1 to 8 C atoms or linear or branched alkoxy having 1 to 8 C atoms and
$R^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxybenzyl)-malonate (for example RonaCare® AP).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such preparations with the compounds according to the invention in percent by weight ratios in the range from 1000:1 to 1:1000, preferably in percent by weight ratios of 100:1 to 1:100.

Of the phenols which can be used in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydoxyflavones. It is observed therein that dihydroxyflavones containing an OH group adjacent to the keto function or OH groups in the 3'4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers and I. M. C. M. Rietjens (Free Radical Biology & Medicine 2001, 31(7), 869-881, have investigated the pH dependence of the antioxidant action of hydroxyflavones. Quercetin exhibits the highest activity amongst the structures investigated over the entire pH range.

Besdies the compounds of the formula (I), the preparations may also comprise one or more further anti-ageing active compounds. Suitable anti-ageing active compounds, in particular for skin-care preparations, are preferably so-called compatible solutes. These are substances which are involved in the osmosis—regulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N.-acetylornithine, trimethylamine N-oxide di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof.

Additionally, anti-aging active compounds which can be used are products from Merck, such as, for example, 5,7-dihydroxy-2-methylchromone, marketed under the trade name RonaCare® Luremine, RonaCare® Isoquercetin, RonaCare® Tilirosid or RonaCare® Cyclopeptide 5.

The preparations may also comprise one or more skin-lightening active compounds or synonymously depigmentation active compounds or melanogenesis inhibitors. Skin-lightening active compounds can in principle be all active compounds known to the person skilled in the art. Examples of compounds having skin-lightening activity are hydroquinone, kojic acid, arbutin, aloesin, niacinamide, azelaic acid, elagic acid, mulberry extract, magnesium ascorbyl phosphate, liquorice extract, emblica, ascorbic acid or rucinol.

Furthermore, the preparations according to the invention may comprise at least one self-tanning substance as further ingredient.

Advantageous self-tanning substances which can be employed are, inter alia: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or combination thereof.

The at least one further self-tanning substance is preferably present in the preparation in an amount of 0.01 to 20% by weight, particularly preferably in an amount of 0.5 to 15% by weight and very particularly preferably in an amount of 1 to 8% by weight, based on the total amount of the preparation.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight. Nutrition-physiological applications are oriented towards the respective recommended vitamin requirement.

The preparations according to the invention may also comprise one or more further anti-cellulite active compounds or slimness active compounds. The retinoids described above are also suitable, for example, as effective anti-cellulite active compounds. Further known anti-cellulite active compounds are phosphodiesterase inhibitors (for example xanthine derivatives, such as theophylline, caffeine, theobromine or aslts thereof, such as aminophylline) and certain oil-soluble plant extracts, such as extracts from common ivy (*Hedera helix*), arnica (*Arnica montana*), rosemary (*Rosmarinus officinalis* N), marigold (*Calendula officinalis*), sage (*Salvia officinalis* N), ginseng (*Panax ginseng*), *Hypericum perforatum*, *Ruscus aculeatus*, *Filipendula ulmaria* L and *Ortosifon stamincus* Benth, and also mixtures of these plant extracts, as disclosed in U.S. Pat. No. 4,795,638.

The xanthine derivative caffeine or theophylline is employed as further anti-cellulite active compound. The xanthine derivatives are typically employed in an amount of 0.05% by weight to 20% by weight, preferably in an amount of 0.10% by weight to 10% by weight and particularly preferably in an amount of 0.5% by weight to 3.0% by weight, based on the total weight of the preparation.

The present invention also relates to a process for the preparation of a preparation, as described above, characterised in that at least one compound of the formula (I) is mixed with a vehicle which is suitable for topical applications or for foods and optionally with assistants and or fillers. Suitable vehicles and assistants or fillers are described in detail in the following part.

The said constituents of the preparation can be incorporated in the usual manner, with the aid of techniques which are well known to the person skilled in the art.

The cosmetic and dermatological preparations can be in various forms. Thus, they can be, for example, a solution, a water-free preparation, an emulsion or microemulsion of the water-in-oil (W/O) type or of the oil-in-water (O/W) type, a multiple emulsion, for example of the water-in-oil-in-water (W/O/W) or O/W/O type, a gel, a solid stick, an ointment or also an aerosol. Preference is given to emulsions. O/W emulsions are particularly preferred. Emulsions, W/O emulsions and O/W emulsions can be obtained in the usual manner.

The following, for example, may be mentioned as application form of the preparations to be employed: solutions, suspensions, emulsions, PIT emulsions, pastes, ointments, gels, creams, lotions, powders, soaps, surfactant-containing cleansing preparations, oils, aerosols plasters, compresses, bandages and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

A preferred solubiliser in general is 2-isopropyl-5-methylcyclohexanecarbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:
mineral oils, mineral waxes
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group branched and unbranched hydrocarbons and hydrocarbon waxes, silicone oils, dialkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

In a preferred embodiment, the preparations to be employed comprise hydrophilic surfactants. The hydrophilic surfactants are preferably selected from the group of the alkylglucosides, acyl lactylates, betaines and coconut amphoacetates.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alchols, cetyl alcohols, cetylstearyl alcohols (cetearyl alcohols).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laurethl-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cprinate, polyethylene glycol (20) glyceryl oleate, polyethylene glycol (20) glyceryl isostearate, polyethylene glycol (18) glyceryl oleate (cocoate).

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty bodies, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oilyalcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is generally made of the customary propellants, such as alkanes, fluoroalkanes and chlorofluoroalkanes, preferably alkanes.

In order that the compounds of the formula (I) are able to develop their positive action on the skin particularly well, it may be preferred to allow the compounds of the formula (I) to penetrate into deeper skin layers. A number of possibilities are available for this purpose. Firstly, the compounds of the formula (I) can have adequate lipophilicity in order to be able to penetrate through the outer skin layer into epidermal layers. As a further possibility, corresponding transport agents, for example liposomes, which facilitate transport of the compounds of the formula (I) through the outer skin layers may also be provided in the preparation. Finally, systemic transport of the compounds of the formula (I) is also conceivable. The preparation is then designed, for example, so that it is suitable for oral administration.

The compounds having the formula (I) can in accordance with the invention also be used in foods or as food supplements or as "functional food". The further explanations given for foods also apply analogously to food supplements and to "functional food".

The foods which can be enriched in accordance with the present invention with one or more compounds of the formula (I) encompass all materials which are suitable for consumption by animals or for consumption by humans, for example vitamins and provitamins thereof, fats, minerals or amino acids". The foods may be solid, but also in liquid form, i.e. in the form of a drink.

Foods which can be enriched in accordance with the present invention with one or more compounds of the formula (I) are, for example, foods which originate from a single natural source (for example sugar, unsweetened juice, corn, cereals, cereal syrup), mixtures of foods of this type (for example multivitamin preparations, mineral mixtures or sweetened juice) or food preparations (for example prepared cereals, biscuits, mixed drinks, foods prepared yoghurt, diet foods, low-calorie foods or animal feeds).

The foods which can be enriched in accordance with the present invention with one or more compounds of the formula (I) thus encompass all edible combinations of carbohydrates, lipids, proteins, inorganic elements, trace elements, vitamins, water or active metabolites of plants and animals.

The foods which can be enriched in accordance with the present invention with one or more compounds of the formula (I) are preferably administered orally, for example in the form of meals, pills, tablets, capsules, powders, syrup, solutions or suspensions.

The foods according to the invention which are enriched with one or more compounds of the formula (I) can be prepared with the aid of techniques which are well known to the person skilled in the art.

In the present invention furthermore also relates to compounds of the formula (Id) to (Ij)

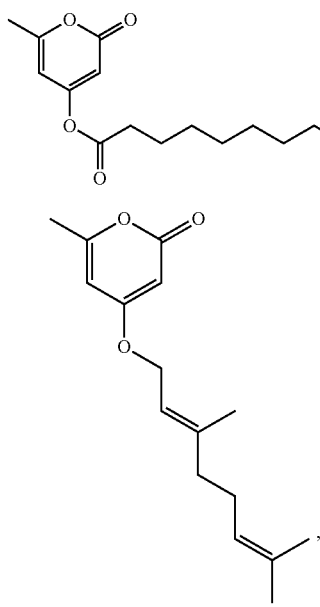

(Id)

(Ie)

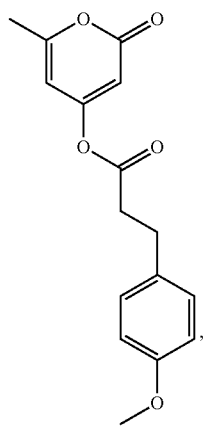

(If)

(Ig)

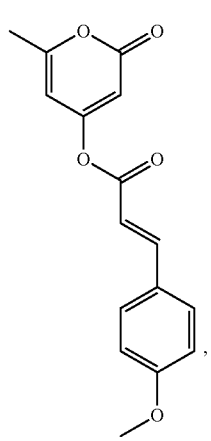

(Ih)

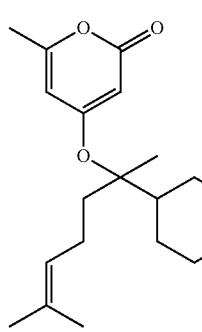

(Ii)

(Ij)

The invention will be explained in greater detail below with reference to examples. the invention can be carried out throughout the range claimed and is not restricted to the examples given here.

EXAMPLES

Example 1: 6-Methyl-4-tetradecyloxy-2-pyrone (Ic)

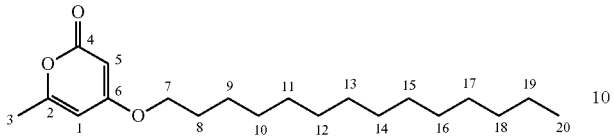

2.50 g (19.8 mmol) of 4-hydroxy-6-methyl-2-pyrone (Ia) and 3.30 ml (23.8 mmol) of triethylamine are initially introduced in 12.5 ml of acetonitrile. The mixture is heated to 82° C., and 6.50 ml (23.8 mmol) of 1-bromotetradecane is added at this temperature. The milky-yellow solution is then boiled under reflux for 16 h. After 4 h, a white solid starts to precipitate out. The testing for complete reaction conversion was carried out by TLC analysis (dichloromethane/methanol 9:1). Cooling of the suspension to RT causes so much solid to precipitate out that the mixture becomes solid. The mixture is diluted with acetonitrile in order to make it stirrable, the solid is filtered off with suction via a suction filter, rinsed with acetonitrile and dried in vacuo at RT. The solid obtained is recrystallised from ethanol.

Yield: 2.20 g=34.4% of theory
Colour: white
Empirical formula: $C_{20}H_{34}O_3$
Molecular weight: 322.5 g/mol
Analysis:
MS (EI): m/e (relative intensity, %)=322 ([M+] 14)
$^1$H-NMR (CDCl$_3$, 400 MHz): δ=5.78-5.76 (m, 1H, H-1), 5.37 (d, 1H, J=2.1 Hz, H-5), 3.92 (t, 2H, J=6.5 Hz, H-7), 2.20 (s, 3H, H-3), 1.80-1.71 (m, 2H, H-8), 1.50-1.17 (m, 22H, H-9 to H-19), 0.88 (t, 3H, J=6.7 Hz, H-20)

Example 2: 4-Hexadecanoyloxy-6-methyl-2-pyrone (Id)

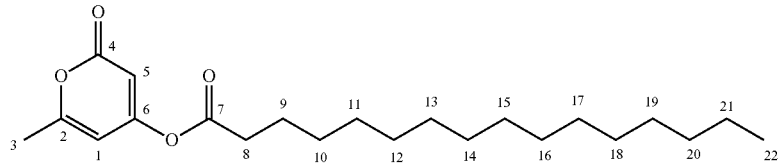 [SMILES: CCCCCCCCCCCCCCCC(=O)Oc1cc(C)oc(=O)c1]

5.00 g (39.6 mmol) of 4-hydroxy-6-methyl-2-pyrone (Ia) and 4.40 g (39.6 mmol) of potassium tert-butoxide are initially introduced in 100 ml of N,N-dimethylformamide. 13.2 ml (43.6 mmol) of palmitoyl chloride is then added dropwise to the dark-yellow suspension at RT, and the solution, which is now pale yellow, is stirred at RT for 16 h. A reaction check using TLC (eluent: dichloromethane/methanol 9:1) shows complete conversion. Water is added to the reaction mixture, during which solid precipitates out. The mixture is stirred for a further 30 min, the solid is then filtered off with suction via a suction filter, rinsed with water and dried in vacuo at 40° C. The purification is carried out by crystallisation from ethanol.

Yield: 4.00 g=27.7% of theory
Colour: yellowish
Empirical formula: $C_{22}H_{36}O_4$
Molecular weight: 364.5 g/mol Analysis:
MS (EI): m/e (relative intensity, %)=364 ([M+] 3)
$^1$H-NMR (CDCl$_3$, 400 MHz): δ=6.04-6.02 (m, 1H, H-1), 5.96-5.94 (m, 1H, H-5), 2.52 (t, 2H, J=7.5 Hz, H-8), 2.26 (s, 3H, H-3), 1.70 (quint, 2H, J=7.4 Hz, H-9), 1.43-1.19 (m, 24H, H-10 to H-21), 0.88 (t, 3H, J=6.7 Hz, H-22).

Example 3: 4-((E)-3,7-Dimethylocta-2,6-dienyloxy)-6-methyl-2-pyrone (Ie)

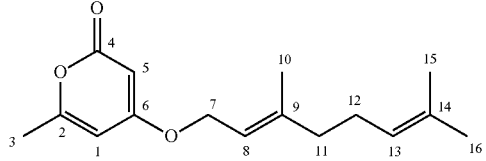

5.00 g (39.6 mmol) of 4-hydroxy-6-methyl-2-pyrone and 6.60 g (43.6 mmol) of 1,8-diazabicyclo[5.4.0]undec-7-ene (DBU) are initially introduced in 80.0 ml of acetonitrile and heated to 80° C. 7.90 ml (39.6 mmol) of (E)-1-bromo-3,7-dimethylocta-2,6-diene is then carefully added and heated under reflux for 40 h. The testing for complete reaction conversion is carried out by TLC analysis (toluene/ethyl acetate 4:1). The reaction mixture is evaporated to dryness and purified by chromatography with toluene/ethyl acetate 9:1.

Yield: 1.0 g=9.6% of theory
Colour: colourless
Empirical formula: $C_{16}H_{22}O_3$
Molecular weight: 262.3 g/mol
Analysis:
MS (EI): m/e (relative intensity, %)=262 ([M+] 4)
$^1$H-NMR (CDCl$_3$, 500 MHz): δ=5.79-5.75 (m, 1H, H-1), 5.41-5.37 (m, 2H, H-5+H-8), 5.12-5.05 (m, 1H, H-13), 4.51 (d, 2H, J=6.8 Hz, H-7), 2.19 (s, 3H, H-3), 2.14-2.03 (m, 4H, H-11+H-12), [1.71 (s, 3H), 1.68 (s, 3H), 1.60 (s, 3H)] H-10+H-15+H-16.
$^{13}$C-NMR (DMSO, 300 MHz): δ=170.5 (C-4), 165.2 (C-2 or C-6), 160.4 (C-2 or C-6), 143.5 (C-9), 132.1 (C-14), 123.3 (C-13), 117.2 (C-8), 100.7 (C-1), 88.0 (C-5), 65.7 (C-7), 39.5 (C-11), 26.2 (C-12), 25.7 (C-16), 19.8 (C-3), 17.7 (C-15), 16.7 (C-10).

Example 4: 3-((E)-3,7-Dimethylocta-2,6-dienyl)-4-hydroxy-6-methyl-2-pyrone (Ii)

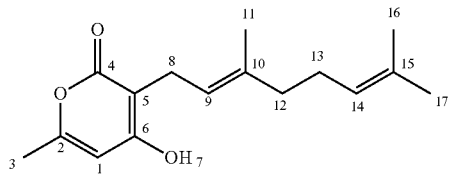

5.00 g (39.6 mmol) of 4-hydroxy-6-methyl-2-pyrone and 6.60 g (43.6 mmol) of DBU are initially introduced in 80.0 ml of acetonitrile and heated to 80° C. 7.90 ml (39.6 mmol) of (E)-1-bromo-3,7-dimethylocta-2,6-diene is then carefully added and heated under reflux for 40 h. The conversion is checked using TLC (eluent: toluene/ethyl acetate 4:1). The reaction mixture is evaporated to dryness, purified by chromatography with toluene/ethyl acetate 4:1, then with ethyl acetate/ethanol 1:1.

Yield: 1.60 g=15.4% of theory

Colour: yellow

Empirical formula: $C_{16}H_{22}O_3$

Molecular weight: 262.3 g/mol

Analysis:

MS (EI): m/e (relative intensity, %)=262 ([M+] 23)

$^1$H-NMR (DMSO, 500 MHz): δ=14.49 (s, 1H, H-7), 5.98 (s, 1H, H-1), 5.13-5.07 (m, 1H, H-9), 5.06-5.00 (m, 1H, H-14), 2.95 (d, 2H, J=7.1 Hz, H-8), 2.11 (s, 3H, H-3), 1.99 (q, 2H, J=7.0 Hz, H-13), 1.89 (t, 2H, J=7.0 Hz, H-12), [1.65 (s, 3H), 1.59 (s, 3H), 1.52 (s, 3H)] H-11+H-16+H-17.

$^{13}$C-NMR (DMSO, 300 MHz): δ=164.6 (C-4+C-6), 159.7 (C-2), 134.4 (C-10), 130.6 (C-15), 124.1 (C-14), 121.6 (C-9), 100.6 (C-5), 99.8 (C-1), 38.7 (C-12), 26.1 (C-13), 25.4 (C-17), 21.6 (C-8), 19.2 (C-3), 17.5 (C-16), 15.9 (C-11).

Example 5: 4-Ethanoyloxy-6-methyl-2-pyrone

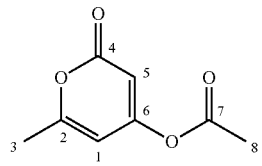

2.00 g (15.9 mmol) of 4-hydroxy-6-methyl-2-pyrone and 1.50 ml (15.9 mmol) of acetic anhydride are suspended in 16.0 ml of toluene, and 16.0 µl (0.30 mmol) of sulfuric acid are added. The suspension is stirred at RT for 16 h, the conversion is checked using TLC (eluent: ethyl acetate/heptane 2:1). The solid (corresponds to the starting material) is filtered off with suction, the mother liquor is evaporated in a rotary evaporator. The residue obtained is purified by column chromatography with ethyl acetate/heptane 2:3.

Yield: 1.20 g=45.0% of theory

Colour: yellowish

Empirical formula: $C_8H_8O_4$

Molecular weight: 168.1 g/mol

Analysis:

MS (EI): m/e (relative intensity, %)=168 ([M+] 28)

$^1$H-NMR (DMSO, 400 MHz): δ=6.30-6.28 (m, 1H, H-1), 6.05-6.02 (m, 1H, H-5), 2.27 (s, 3H, H-3), 2.25-2.23 (m, 3H, H-8).

$^{13}$C-NMR (DMSO, 300 MHz): δ=167.2 (C-4), 163.7 (C-2 or C-6), 163.5 (C-2 or C-6), 162.8 (C-7), 101.5 (C-5), 100.6 (C-1), 20.9 (C-8), 19.4 (C-3).

Example 6: 4-(2-Ethylhexanoyloxy)-6-methyl-2-pyrone

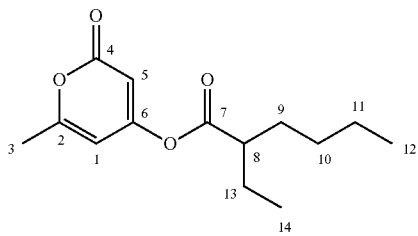 [SMILES: CCCCC(CC)C(=O)Oc1cc(C)oc(=O)c1]

2.50 g (19.8 mmol) of 4-hydroxy-6-methyl-2-pyrone and 2.20 g (19.8 mmol) of potassium tert-butoxide are initially introduced in 50.0 ml of N,N-dimethylformamide. 3.50 g (21.8 mmol) of 2-ethylhexanoyl chloride is then added dropwise to the dark-yellow suspension at RT. The reaction mixture is stirred at RT for 16 h. A reaction check using TLC (eluent: dichloromethane/methanol 9:1) shows complete conversion. Water and tert-butyl methyl ether (MtB ether) are added to the reaction mixture. The phases are separated, the aqueous phase is extracted with MtB ether, the combined organic phases were washed with water, dried over sodium sulfate, filtered and evaporated in a rotary evaporator. The residue is purified by column chromatography with ethyl acetate/heptane 2:1.

Yield: 4.10 g=82.0% of theory

Colour: yellowish

Empirical formula: $C_{14}H_{20}O_4$

Molecular weight: 252.3 g/mol

Analysis:

MS (EI): m/e (relative intensity, %)=252 ([M+] 7)

$^1$H-NMR (DMSO, 400 MHz): δ=6.27-6.24 (m, 1H, H-1), 6.03-6.01 (m, 1H H-5), 2.56-2.47 (m, 1H, H-8), 2.26 (s, 3H, H-3), 1.72-1.41 (m, 4H, H-9+H-13), 1.39-1.18 (m, 4H, H-10+H-11), 0.97-0.81 (m, 6H, H-12+H-14) $^{13}$C-NMR (DMSO, 300 MHz): δ=172.5 (C-4), 163.7+163.3+163.2 (C-2+C-6+C-7), 101.4 (C-1), 101.0 (C-5), 47.4 (C-8), 31.3 (C-9), 29.5 (C-10), 25.2 (C-13), 22.5 (C-11), 20.0 (C-3), 13.8 (C-12), 11.7 (C-14).

Example 7: 4-(1-Ethylpentyloxy)-6-methyl-2-pyrone (Ij)

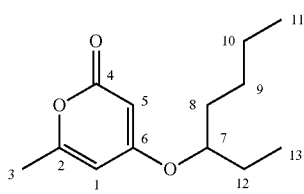

2.50 g (19.8 mmol) of 4-hydroxy-6-methyl-2-pyrone and 3.30 ml (23.8 mmol) of triethylamine are initially introduced in 12.5 ml of acetonitrile. The mixture is heated to 82° C., and 3.90 g (21.8 mmol) of 3-bromoheptane was added at this temperature. The orange-yellow solution is then boiled under reflux for 16 h. The testing for complete reaction conversion is carried out by TLC analysis (dichloromethane/methanol 9:1). The reaction mixture is evaporated to dryness in a rotary evaporator, the subsequent purification is carried out by column chromatography with ethyl acetate/heptane 2:1.

Yield: 1.40 g=31.5% of theory
Colour: yellowish
Empirical formula: $C_{13}H_{20}O_3$
Molecular weight: 224.3 g/mol Analysis:

MS (EI): m/e (relative intensity, %)=224 ([M+] 15)

$^1$H-NMR (DMSO, 400 MHz): δ=5.90-5.87 (m, 1H, H-1), 5.52 (d, 1H, J=2.2 Hz, H-5), 4.42 (quint, 1H, J=5.9 Hz, H-7), 2.16 (s, 3H, H-3), 1.69-1.52 (m, 4H, H-8+H-12), 1.36-1.19 (m, 4H, H-9+H-10), 0.93-0.83 (m, 6H, H-11+H-13).

$^{13}$C-NMR (DMSO, 300 MHz): δ=170.2 (C-4), 165.3 (C-2 or C-6), 162.0 (C-2 or C-6), 101.0 (C-1), 87.9 (C-5), 80.3 (C-7), 32.5 (C-8), 27.3 (C-9), 26.1 (C-12), 22.8 (C-10), 19.7 (C-3), 13.9 (C-11), 9.3 (C-13).

Example 8: cDNA Array

The assay is carried out using primary epidermal keratinocytes. After incubation at 37° C. and in a 5% $CO_2$ atmosphere for 48 hours, the culture medium (DPBS and HyQtase cell detachment solution) is removed, and the test substances 4-hydroxy-6-methyl-2-pyrone Ia (40 μM) and 3-((E)-3,7-dimethylocta-2,6-dienyl)-4-hydroxy-6-methyl-2-pyrone Ii (50 □M) in assay medium (keratinocytes basal medium M2 and supplement mix) are added. All-trans retinoic acid is used as positive control. The cells are then cultured at 37° C. and under 5% $CO_2$ for 24 hours.

The mRNA is isolated using the RNEASY Minikit test kit from Qiagen in accordance with the instruction manual. 1 μg of the RNA is then in each case converted into cDNA with the aid of the Firsts Strand cDNA synthesis kit from Roche. The 20 μl of cDNA obtained are diluted 1/10, and 110 μl of TaqMan™ Universal PCR Master Mix are in each case added to 110 μl of the cDNA samples. 100 μl are pipetted per slot into the Custom TaqMan™ array cards. The cards are sealed, centrifuged and then measured using the TaqMan™ 7900HT. The values obtained are standardised. Values less than or equal to −1.5 indicate moderate to strong downregulation of the expression of the genes investigated.

The influences of hydroxy-6-methyl-2-pyrone Ia (40 μM) and 3-((E)-3,7-dimethylocta-2,6-dienyl)-4-hydroxy-6-methyl-2-pyrone Ii (50 □M) on the gene expression of the cell envelope proteins calmodulin-like protein (CALML5), filaggrin (FLG), involucrin (IVL), loricrin (LOR), repetin (RPTN), calgranulin A and B (S100A8, S100A9) and transglutaminase 1 (TGM1) are shown in Table 1.

TABLE 1

| Application | CALML5 | FLG | IVL | LOR |
|---|---|---|---|---|
| all-trans retinoic acid (5 μM) | −2.93 | −3.20 | −4.05 | −7.01 |
| Ia (40 μM) | −3.14 | 1.01 | −1.76 | −4.56 |
| Ii (50 μM) | −2.58 | −4.67 | −3.82 | −1.59 |
|  | RPTN | S100A8 | S100A9 | TGM1 |
| all-trans retinoic acid (5 μM) | −2.56 | −3.26 | −3.49 | −3.56 |
| Ia(40 μM) | −3.33 | −1.74 | −2.18 | −1.26 |
| Ii (50 μM) | 1.57 | −2.93 | −1.48 | −1.56 |

For hydroxy-6-methyl-2-pyrone Ia (40 μM), the table shows an inhibiting action of mRNA production for the cornified envelope, apart from filaggrin. Compound Ii also exhibits uniform downregulation of gene expression, apart from repetin. The comparison all-trans retinoic acid exhibits a homogeneous picture of the reduction of mRNA for all cell envelope proteins. The downregulation of this gene family is a typical feature of substances which have an antidifferentiating action.

A second group of genes (Table 2) considered encodes for proteins which correlate with cell-cell connections. Corneodesmosin (CDSN), desmoglein 1 (DSG1), desmoplakin (DSP) and desmocollin 3 (DSC3) are tested, the associated regulation factors are shown in Table 2. The expression of all genes is downregulated by Ia and Ii. The downregulation of this protein family is known for retinoids.

TABLE 2

| Application | CDSN | DSC3 | DSG1 | DSP |
|---|---|---|---|---|
| all-trans retinoic acid (μM) | −2.37 | −1.23 | −9.22 | −1.56 |
| 4-Hydroxy-6-methyl-2-pyrone Ia (40 μM) | −2.14 | −1.69 | −1.39 | −1.40 |
| 3-((E)-3,7-Dimethylocta-2,6-dienyl)-4-hydroxy-6-methyl-2-pyrone Ii (50 μM) | −13.20 | −1.14 | −8.20 | −1.53 |

The results of the cDNA array show a similar expression pattern to retinoic acid.

Example 9: Ex-Vivo Study

Histological explants having an average diameter of 10 mm from the lower abdomen tissue of a 45-year-old European woman are prepared. The pieces of tissue are stored in BEM medium in a moist, 5% $CO_2$ atmosphere at 37° C. The tissue is divided into 3 batches of 6 explants each.

Test Substances and Sampling

| | Application | Sampling |
|---|---|---|
| K | — | Day 8 |
| V | Mygliol/ethanol (80/20) | Day 8 |
| P | 4-Hydroxy-6-methyl-2-pyrone Ia (1% in Mygliol/ethanol 80/20) | Day 8 |

Batch K represents the negative control. Only the vehicle is applied to batch V. Batch P is treated with 4-hydroxy-6-methyl-2-pyrone Ia (1% in Mygliol/ethanol 80/20). 30 μl of the 1% substance solutions in Myliol/ethanol (80/20) are applied using a round filter paper and allowed to act for 2 hours. Applications are carried out on day 0, 1, 4, 6 and 7.

On the 8th day, 3 pieces of tissue from each batch are fixed in Bouin solution. After fixing for 48 hours, the samples are dehydrated by means of Leica TP 1020 and soaked in paraffin. Tissue sections with a thickness of 5 μm are produced from the paraffin blocks using a microtome and mounted on Superfrost specimen slides. The microscopic investigation is carried out using a Leica Orthoplan microscope after the tissue sections mounted on specimen slides have been stained with Masson-Goldner trichrome stain. In order to be able to assess the effect of the substances, the thickness of the epidermis or the change thereof is measured.

Results: on day 0, the skin explants employed are investigated morphologically, and the test substances are then applied topically for the first time. The general morphology of the skin sections shows a moderately thick stratum corneum.

After 8 days, the morphology of the untreated skin (batch K) is virtually unchanged.

The skin tissue exposed to the vehicle (batch V) exhibits only a slight change in the stratum granulosum and a reduction in the parakeratosis which is present in untreated skin.

Treatment with substance Ia (batch P) induces moderate growth of the epidermis. Compared with the vehicle, a 10% thicker epidermis is measured on the 8th day after exposure to compound Ia. The collagen network in the dermis along the dermo-epidermal junction zone becomes denser.

Example 10: Lipolysis

The study is carried out using normal human adipocytes originating from the lower abdomen biopsy of a 31-year-old woman. The hypodermis is isolated from the biopsy and incubated at 37° C. for 30 minutes with collagenase solution. The separated adipocytes are washed and diluted with assay medium (MEM without Phenol Red, penicillin 25 UI/ml/ streptomycin 25 µl/ml, L-glutamine 2 mM, bovine serum albumin (BSA), fatty acid-free: 0.5% (p/v)).

The test solutions or the caffeine reference are added to the cell suspensions, and the mixtures are incubated at 37° C. and in a 5% $CO_2$ atmosphere for 2 hours. The pyrones tested and concentrations are indicated in the table.

After this time, the unesterified fatty acids liberated from the samples are quantified.

The measurement is carried out using a Wako NEFA-C test kit in accordance with the instruction manual.

Test Substances and Concentrations for Lipolysis

| Test substance | Test concentrations |
| --- | --- |
| Caffeine | 1 mM |
| 4-Methoxy-6-methyl-2-pyrone Ib | 0.25 mM; 0.5 mM; 1 mM and 2 mM |
| 3-((E)-3,7-Dimethyl-octa-2,6-dienyl)-4-hydroxy-6-methyl-2-pyrone Ii | 0.25 mM; 0.5 mM; 1 mM and 2 mM |
| 4-(1-Ethylpentyloxy)-6-methyl-2-pyrone Ij | 0.25 mM; 0.5 mM; 1 mM and 2 mM |

Results: compound Ib promotes triacylglycerin degradation (82% stimulation significant at 2 mM). Compound Ij exhibits a similar course (57% stimulation significant at 2 mM). Both substances increase the lipolytic activity as a function of concentration.

The results for compound Ii (−67% (at 2 mM) or −60% (at 1 mM)) indicate that compound Ii is able to counter the breakdown of subcutaneous fatty tissue which begins during skin ageing (filling effect for antiageing).

Example 11: O/W formulation

| Constituents/trade name | Source of supply | INCI | [wt-%] |
| --- | --- | --- | --- |
| A | | | |
| Marlipal 1618/11 | (1) | CETEARETH-11 | 3 |
| Lanette O | (2) | CETEARYLALCOHOL | 7 |
| Luvitol EHO | (3) | CETEARYLOCTANOATE | 5 |
| Tegosoft TN | (4) | C12-15 ALKYLBENZOATE | 2.5 |
| Miglyol 812 N | (1) | CAPRYLIC/CAPRIC TRIGLYCERIDE | 2.5 |
| Propyl 4-hydroxybenzoate | (5) | PROPYLPARABEN | 0.05 |
| 3-((E)-3,7-Dimethylocta-2,6-dienyl)-4-hydroxy-6-methyl-2-pyrone | | | 0.05 |
| B | | | |
| 1,2-Propanediol | (5) | PROPYLENE GLYCOL | 4 |
| Methyl 4-hydroxybenzoate | (5) | METHYLPARABEN | 0.15 |
| Water, demineralised | | AQUA (WATER) | to 100 |
| Water, demineralised | | | 10 |
| Total | | | 100.00 |

Preparation Process:

Firstly, phase A is warmed to 75° C. and phase B to 80° C. Phase B is then slowly added to phase A with stirring and stirred until a homogeneous mixture forms.

Sources of Supply:

(1) Sasol Germany GmbH (2) Cognis GmbH (3) BASF AG (4) Degussa-Goldschmidt AG (5) Merck KGaA/Rona®

Example 12: O/WW Formulation

| Constituents/trade name | Source of supply | INCI | [wt-%] |
| --- | --- | --- | --- |
| A | | | |
| Marlipal 1618/11 | (1) | CETEARETH-11 | 3 |
| Lanette O | (2) | CETEARYLALCOHOL | 7 |
| Luvitol EHO | (3) | CETEARYLOCTANOATE | 5 |
| Tegosoft TN | (4) | C12-15 ALKYLBENZOATE | 2.5 |
| Miglyol 812 N | (1) | CAPRYLIC/CAPRIC TRIGLYCERIDE | 2.5 |
| Propyl 4-hydroxybenzoate | (5) | PROPYLPARABEN | 0.05 |
| Retinol | (3) | (2E,4E,6E,8E)-3,7-Dimethyl-9-(2,6,6-trimethylcyclohex-1-enyl)nona-2,4,6,8-tetraen-1-ol | 0.04 |
| 3-((E)-3,7-Dimethylocta-2,6-dienyl)-4-hydroxy-6-methyl-2-pyrone (Ii) | | | 0.1 |
| B | | | |
| 1,2-Propanediol | (5) | PROPYLENE GLYCOL | 4 |
| Methyl 4-hydroxybenzoate | (5) | METHYLPARABEN | 0.15 |
| Water, demineralised | | AQUA (WATER) | to 100 |
| Water, demineralised | | | 10 |
| Total | | | 100.00 |

Preparation Process:

Firstly, phase A is warmed to 75° C. and phase B to 80° C. Phase B is then slowly added to phase A with stirring and stirred until a homogeneous mixture forms.

Sources of supply:
(1) Sasol Germany GmbH (2) Cognis GmbH (3) BASF AG (4) Degussa-Goldschmidt AG (5) Merck KGaA/Rona®

Example 13: O/W Formulation

| Constituents/trade name | Source of supply | INCI | [wt-%] |
|---|---|---|---|
| A | | | |
| Tego Care 150 | (1) | GLYCERYL STEARATE, STEARETH-25, CETETH-20, STEARYL ALCOHOL | 8 |
| Lanette O | (2) | CETEARYL ALCOHOL | 1.5 |
| Luvitol EHO | (3) | CETEARYL OCTANOATE | 5 |
| Miglyol 812 N | (4) | CAPRYLIC/CAPRIC TRIGLYCERIDE | 5 |
| Paraffin liquid | (5) | PARAFFINUM LIQUIDUM (MINERAL OIL) | 3 |
| AbilWax 2434 | (1) | STEAROXY DIMETHICONE | 1.6 |
| Dow Corning 200 Fluid (350 cs) | (6) | DIMETHICONE | 0.5 |
| Propyl 4-hydroxybenzoate | (5) | PROPYLLPARABEN | 0.05 |
| B | | | |
| 1,2-Propanediol | (5) | PROPYLENE GLYCOL | 3 |
| Methyl 4-hydroxybenzoate | (5) | METHYLPARABEN | 0.15 |
| Water, demineralised | | AQUA (WATER) | to 100 |
| C | | | |
| Probiol L 05018 (Empty liposomes) | (7) | AQUA, ALCOHOL DENAT, LECITHIN, GLYCERINE, DISODIUM PHOSPHATE | 5 |
| Water, demineralised | | AQUA (WATER) | 10.00 |
| 4-Hydroxy-6-methyl-2-pyrone | | | 1 |
| Total | | | 100.00 |

Preparation Process:
Firstly, phases A and B are warmed to 80° C. Phase B is then slowly added to phase A with stirring and homogenised. The mixture is then cooled, and phase C is added at 40° C.

Sources of Supply:
(1) Degussa-Goldschmidt AG, (2) Cognis GmbH, (3) BASF AG, (4) Sasol Germany GmbH, (5) Merck KGaA/Rona®, (6) Dow Corning, (7) Kuhs GmbH & Co. KG Example 14: W/O formulation

| Constituents/trade name | Source of supply | INCI | [wt-%] |
|---|---|---|---|
| A | | | |
| Dow Corning 3225 C | (1) | CYCLOMETHICONE, DIMETHICONE COPOLYOL | 23.6 |
| Propyl 4-hydroxybenzoate | (2) | PROPYLPARABEN | 0.05 |
| 4-Hydroxy-6-methyl-2-pyrone | | | 1 |
| B | | | |
| Methyl 4-hydroxybenzoate | (2) | METHYLPARABEN | 0.15 |
| 1,2-Propanediol | (2) | PROPYLENE GLYCOL | 35.9 |
| Water, demineralised | | AQUA (WATER) | to 100 |
| Total | | | 100.00 |

Preparation Process:
Firstly, phase B is dissolved and then added to phase A. The pH is adjusted to the value pH=6.0 using sodium hydroxide solution or citric acid.

Sources of Supply:
(1) Dow Corning (2) Merck KGaA/Rona®

Example 15: O/W Antiageing Cream with UV A/B Protection

| Constituents/trade name | Source of supply | INCI | [wt-%] |
|---|---|---|---|
| A | | | |
| Eusolex® 2292 | (1) | ETHYLHEXYL METHOXYCINNAMATE, BHT | 3 |
| Eusolex® 4360 | (1) | BENZOPHENONE-3 | 0.5 |
| Tego Care 150 | (2) | GLYCERYL STEARATE, STEARETH-25, CETETH-20, STEARYL ALCOHOL | 8 |
| Lanette O | (3) | CETEARYL ALCOHOL | 1.5 |
| Luvitol EHO | (4) | CETEARYL OCTANOATE | 5 |
| Miglyol 812 N | (5) | CAPRYLIC/CAPRIC TRIGLYCERIDE | 5 |
| Paraffin liquid | (1) | PARAFFINUM LIQUIDUM (MINERAL OIL) | 3 |
| Abil-Wax 2434 | (2) | STEAROXY DIMETHICONE | 1.6 |
| Dow Corning 200 Fluid (350 cs) | (6) | DIMETHICONE | 0.5 |
| Propyl 4-hydroxybenzoate | (1) | PROPYLPARABEN | 0.05 |
| 3-((E)-3,7-Dimethylocta-2,6-dienyl)-4-hydroxy-6-methyl-2-pyrone (Ii) | | | 1 |
| B | | | |
| 1,2-Propanediol | (1) | PROPYLENE GLYCOL | 3 |
| Methyl 4-hydroxybenzoate sodium salt | (1) | SODIUM METHYLPARABEN | 0.17 |
| Water, demineralised | | AQUA (WATER) | to 100 |
| Total | | | 100.00 |

Preparation Process:
Firstly, phases A and B are mixed separately and warmed to 80° C. Phase B is then slowly added to phase A with stirring. The mixture is homogenised cooled to room temperature.

Sources of Supply:

(1) Merck KGaA/Rona®, (2) Degussa-Goldschmidt AG, (3) Cognis GmbH, (4) BASF AG, (5) Sasol Germany GmbH, (6)

Example 16: Anticellulite Cream

| Constituents | % |
|---|---|
| A | |
| Cetyl alcohol | 2 |
| Glyceryl Stearate | 5 |
| Caprylic/Capric Triglyceride | 8 |
| Isopropyl Palmitate | 9 |
| 4-methoxy-6-methyl-2-pyrone | 1 |
| B | |
| Glycerin | 3 |
| Preservatives (Germaben II) | 0.8 |
| Water, demineralised | to 100 |

Preparation Process:

Firstly, phase B is dissolved and then added to phase A. The pH is adjusted to the value pH=6.0 using sodium hydroxide solution or citric acid.

Use:

Apply to the skin twice daily with vigorous massaging; carry out circular and up and down movements in the process. The treatment can be carried out both on thighs and also buttocks and stomach.

The invention claimed is:

1. A cosmetic or pharmaceutical composition comprising at least one compound of the formula (I)

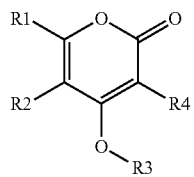

(I)

where
R1 stands for a straight-chain or branched $C_1$- to $C_{20}$-alkyl group,
R2 stands for
H or
straight-chain or branched $C_1$- to $C_{20}$-alkyl group,
R4 stands for
H,
straight-chain or branched $C_1$- to $C_{20}$-alkyl group or
straight-chain or branched $C_2$- to $C_{20}$-alkenyl group having one or more double bonds,
R3 stands for a radical selected from
H,
straight-chain or branched $C_2$- to $C_{20}$-alkyl group,
straight-chain or branched $C_2$- to $C_{20}$-alkenyl group having one or more double bonds, where the alkenyl group may also be substituted by one or more saturated or unsaturated $C_3$- to $C_{12}$-cycloalkyl groups,
straight-chain or branched $C_2$- to $C_{20}$-alkynyl group having one or more triple bonds,
saturated or partially unsaturated non-aromatic $C_3$- to $C_{12}$-cycloalkyl group,
where the rings may in each case also be bridged by —$(CH_2)_n$— groups where n=1 to 3,
an acyl radical of the formula —C(=O)—R6,
R6 stands for
straight-chain or branched $C_1$- to $C_{20}$-alkyl group,
a radical of the formula (II)

(II)

in which X stands for straight-chain or branched $C_1$- to $C_6$-alkylene or straight-chain or branched $C_2$- to $C_6$-alkenylene and the radicals R5 are selected, independently of one another, from H, OH, straight-chain or branched $C_1$- to $C_6$-alkyl or straight-chain or branched O—($C_1$- to $C_6$-alkyl),
at least one vehicle which is suitable for a topical application, and
a further anti-ageing or anti-cellulite active compound; with the proviso that
R4 is a straight-chain or branched $C_2$- to $C_{20}$-alkenyl group having one or more double bonds or
R3 is a straight-chain or branched $C_2$- to $C_{20}$-alkenyl group having one or more double bonds, where the alkenyl group may also be substituted by one or more saturated or unsaturated $C_3$- to $C_{12}$-cycloalkyl groups, straight-chain or branched $C_2$- to $C_{20}$-alkynyl group having one or more triple bonds,
saturated or partially unsaturated non-aromatic $C_3$- to $C_{12}$-cycloalkyl group, where the rings may in each case also be bridged by —$(CH_2)_n$— groups where n=1 to 3, or an acyl radical of the formula —C(=O)—R6.

2. A composition according to claim 1, wherein the at least one compound of the formula (I) is present in an amount of 0.01 to 20% by weight.

3. A process for the preparation of a composition according to claim 1, which comprises mixing the compound of the formula (I) with a vehicle which is suitable for a topical application.

4. A composition according to claim 1, wherein, in formula (I), R1 stands for a straight-chain or branched $C_1$- to $C_6$-alkyl group.

5. A composition according to claim 1, wherein, in formula (I), R2 stands for H or a straight-chain or branched $C_1$- to $C_6$-alkyl group.

6. A composition according to claim 1, wherein, in formula (I), R4 stands for H or a straight-chain or branched $C_2$- to $C_{20}$-alkenyl group having one or more double bonds.

7. A composition according to claim 1, wherein, in formula (I), R3 stands for a radical selected from
H,
straight-chain or branched $C_2$- to $C_{20}$-alkyl group,
straight-chain or branched $C_2$- to $C_{20}$-alkenyl group having one or more double bonds, where the alkenyl group may also be substituted by one or more saturated or partially unsaturated non-aromatic cyclohexyl groups, or
an acyl radical of the formula —C(=O)—R6.

8. A composition according to claim 1, wherein, in formula (I), the radicals R5 are selected, independently of one another, from H, OH or straight-chain or branched O—($C_1$- to $C_6$-alkyl).

9. A composition according to claim 1, wherein, the compound of the formula (I) is selected from the compounds of formulae (Id) to (Ii):

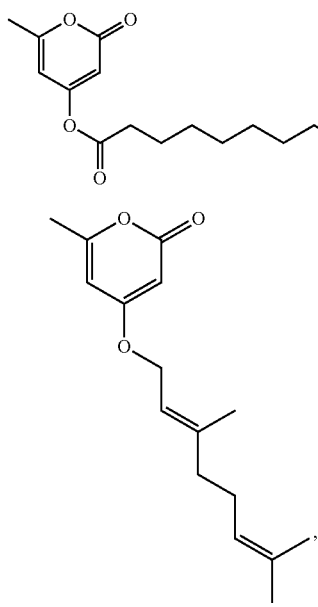

(Id)

(Ie)

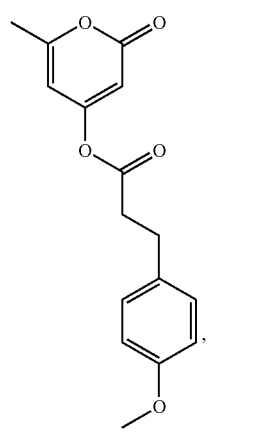

(If)

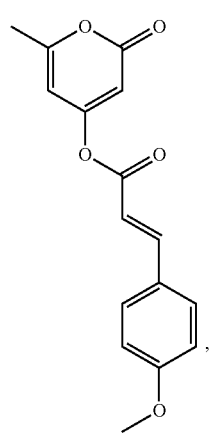

(Ig)

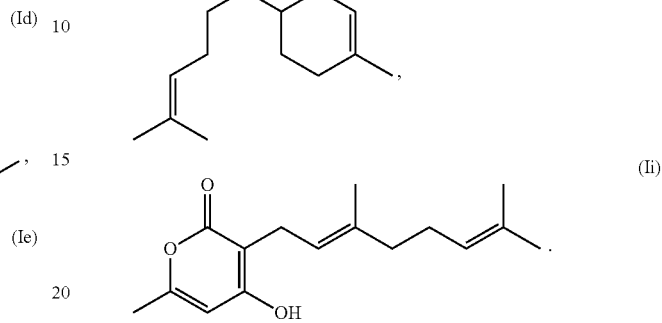

(Ih)

(Ii)

10. A composition according to claim 1, wherein, in formula (I), the radical R3 stands for a radical selected from straight-chain or branched $C_2$- to $C_{20}$-alkenyl group having one or more double bonds, where the alkenyl group may also be substituted by one or more saturated or unsaturated $C_3$- to $C_{12}$-cycloalkyl groups, straight-chain or branched $C_2$- to $C_{20}$-alkynyl group having one or more triple bonds, saturated or partially unsaturated non-aromatic $C_3$- to $C_{12}$-cycloalkyl group, where the rings may in each case also be bridged by —$(CH_2)_n$— groups where n=1 to 3, or an acyl radical of the formula —C(=O)—R6.

11. A compound of one of the formula (Id) to (Ii)

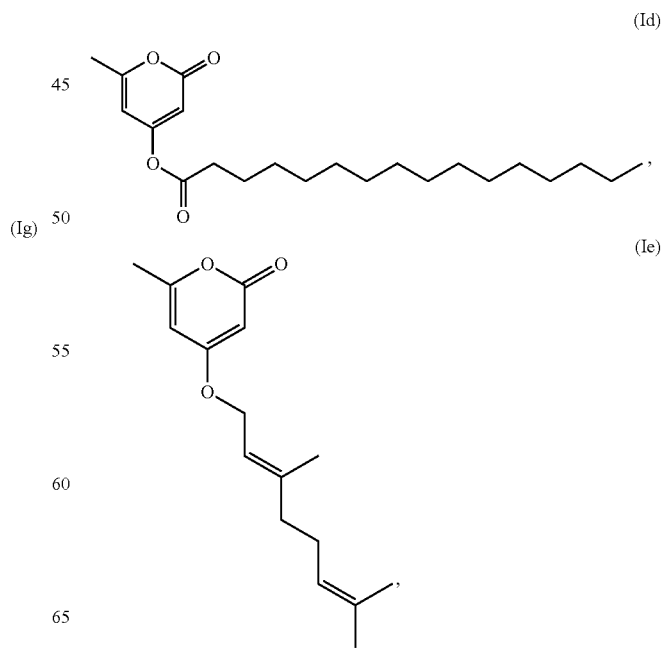

(Id)

(Ie)

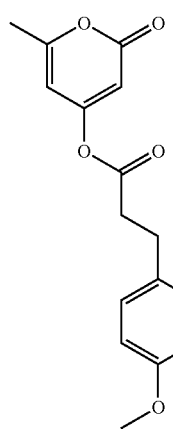
(If)
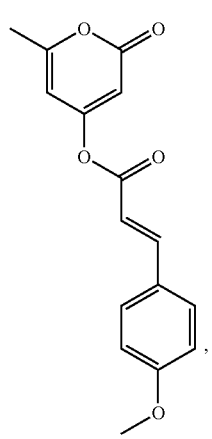
(Ig)
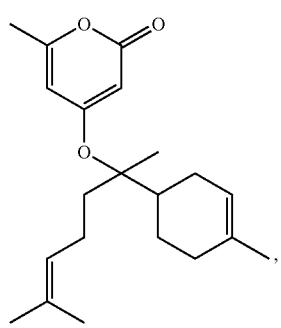
(Ih)
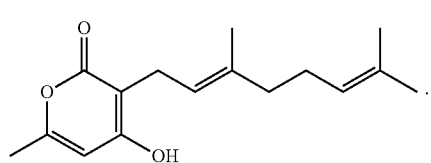
(Ii)
12. A composition according to claim 2, wherein, the compound of the formula (I) is selected from the compounds of the formula (Id) to (Ii):
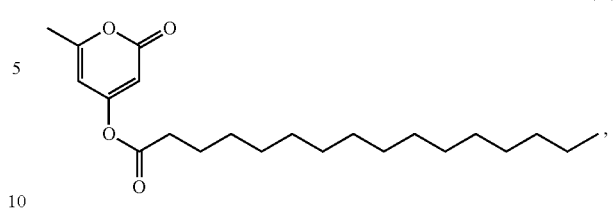
(Id)
(Ie)
(If)
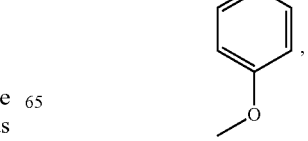
(Ig)

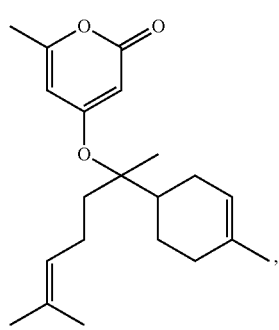
(Ih)
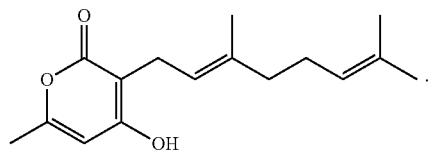
(Ii)
* * * * *